United States Patent [19]
Riazi

[11] Patent Number: 5,674,268
[45] Date of Patent: Oct. 7, 1997

[54] METHOD FOR PROVIDING THERAPEUTIC HEAT TREATMENT AND KIT FOR PRACTICE THEREOF

[75] Inventor: John Riazi, Akron, Ohio

[73] Assignee: The Hygenic Corporation, Akron, Ohio

[21] Appl. No.: 676,428

[22] Filed: Jul. 8, 1996

[51] Int. Cl.$^6$ ........................................... A61F 7/00
[52] U.S. Cl. ........................ 607/96; 607/86; 607/114
[58] Field of Search ................... 607/96, 86, 104, 607/108–112, 114, 80–85, 107; 126/263.01–263.02; 128/898

[56] References Cited

U.S. PATENT DOCUMENTS

| | | | |
|---|---|---|---|
| 2,396,578 | 10/1946 | Kittel et al. | 126/343.5 |
| 3,157,774 | 11/1964 | Moore et al. | 219/326 |
| 3,867,173 | 2/1975 | Putzer | 117/39 |
| 4,632,115 | 12/1986 | Bernardini | 128/370 |
| 4,782,835 | 11/1988 | Bernardini | 607/114 |
| 4,880,415 | 11/1989 | Urakami | 607/111 X |
| 5,213,746 | 5/1993 | Tarwater | 264/221 |
| 5,306,488 | 4/1994 | Vanlerberghe et al. | 424/71 |
| 5,424,519 | 6/1995 | Salee | 219/759 |
| 5,513,629 | 5/1996 | Johnson | 607/114 X |

*Primary Examiner*—Jennifer Bahr
*Assistant Examiner*—Ryan Carter
*Attorney, Agent, or Firm*—Renner, Kenner, Greive, Bobak, Taylor & Weber

[57] ABSTRACT

A method for applying a therapeutic heat treatment to a body part comprises the steps of placing a suitable fluid (20) in a container (10); placing wax (22) in the container; heating the combination (16) of the wax (22) and the fluid (20) until the wax (22) has melted forming a layer and the fluid (20) has reached the treatment temperature; and passing the body part (40) through the layer of wax (46) and into the fluid to form a glove around the body part. The present invention also provides for a kit (60) for providing therapeutic heat treatment, the kit comprising a microwavable container (20) a removable lid (30); and a quantity of wax (22).

19 Claims, 2 Drawing Sheets

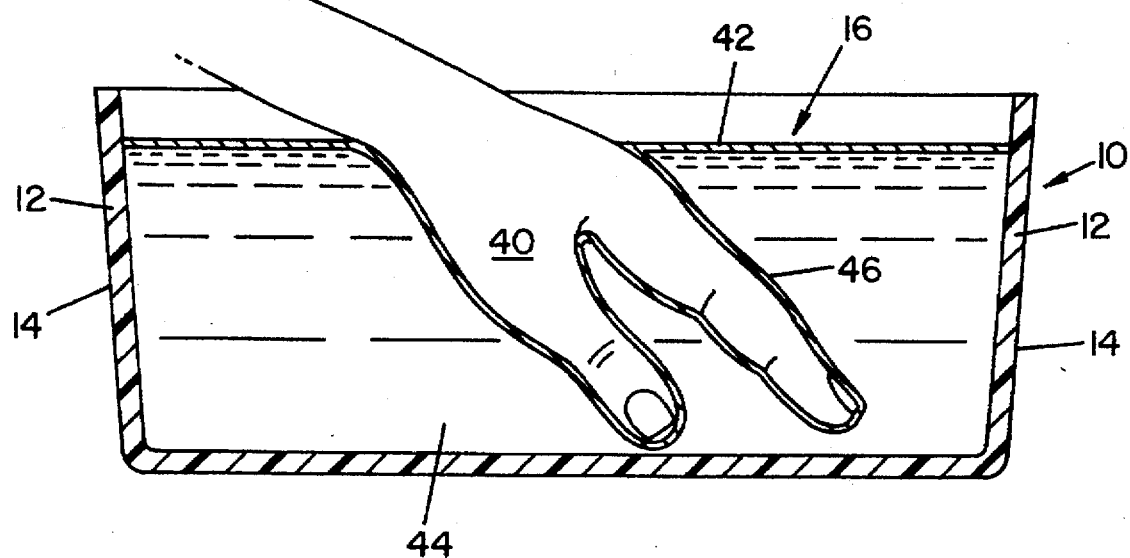
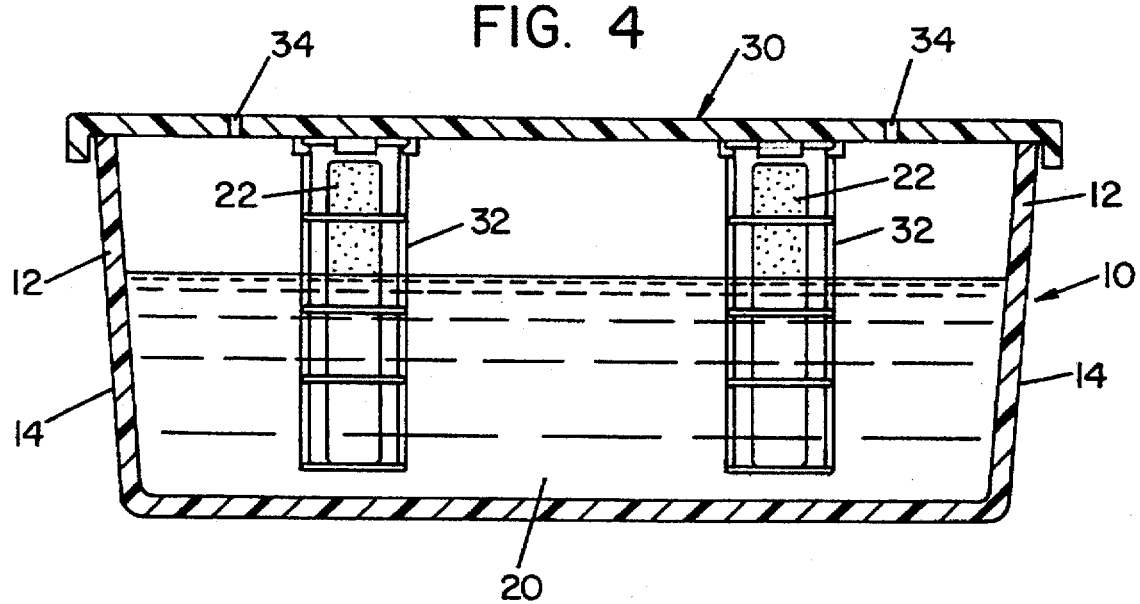

5,674,268

METHOD FOR PROVIDING THERAPEUTIC HEAT TREATMENT AND KIT FOR PRACTICE THEREOF

TECHNICAL FIELD

The present invention generally relates to a method for applying heat to a body extremity for therapeutic purposes. More particularly, the invention relates to a method for providing a heated wax and water combination for applying heat to an extremity. Specifically, the present invention relates to a method for providing a layer of stabilized wax over a body of heated water such that an extremity is coated with wax as it is passed through the wax into the water where the wax-coated extremity is subjected to the heat from the water.

BACKGROUND OF THE INVENTION

Subjecting a body part, or extremity, such as a hand or a foot to heat has long been known to be therapeutic for ailments such as arthritis and the like. One known method for subjecting an extremity to a heat treatment is to provide a quantity of stabilized heated wax into which the extremity is immersed. The extremity is then removed and allowed to cool for twenty to thirty seconds. The extremity is then immersed again and removed. The immersions are repeated until approximately one eighth of an inch of wax has covered the entire extremity. The extremity is then wrapped in a towel and the wax is allowed to cool. While the wax is cooling, the extremity is subjected to the heat from the wax for approximately fifteen minutes. When the wax on the extremity has cooled, the wax is peeled off and may be discarded.

Such a wax treatment requires approximately six pounds of wax to create the volume necessary to adequately cover the extremity. For instance, if the wax treatment is going to be used on a hand, the stabilized heated wax must be deep enough to cover the hand up to the wrist. The large quantity of wax requires a significant amount of time to reach the treatment temperature and to stabilize. The wax is typically heated in an electric pot until the entire volume of wax has reached the desired treatment temperature of approximately 130 degrees Fahrenheit. The process of heating and stabilizing the wax may take six to eight hours.

One problem with this method of treatment is the length of time to heat and stabilize the wax. Patients desiring the therapeutic heat treatment, and more particularly their caregivers, desire to have such a treatment on demand instead of having to plan ahead for heating the wax. Another undesirable aspect of the treatment is the amount of wax that is used to coat the extremity. In a typical treatment on a hand, approximately 50 to 60 grams of wax is used to coat the hand. This wax may be discarded when the wax has cooled after the treatment. Additionally, the 6 to 8 pounds of wax must be periodically discarded or cleaned. An additional problem with this method is that an electric heater is typically used to heat the wax. Although safely designed, electric heaters generally increase the risks of user injury and increase the possibility of fires when left on for the lengths of time necessary to heat and stabilize the wax.

SUMMARY OF THE INVENTION

It is, therefore, a primary object of the present invention to provide a therapeutic heat treatment method requiring a relatively short amount of time to prepare.

It is another object of the present invention to provide a method for providing a therapeutic heat treatment requiring a relatively small quantity of wax.

It is still another object of the present invention to provide a therapeutic heat treatment that may be safely prepared in a microwave oven.

It is yet another object of the present invention to provide a therapeutic heat treatment using a relatively low volume of wax and a relatively high volume of heated water.

It is a further object of the present invention to provide a therapeutic heat treatment where a relatively thin layer of stabilized wax floats on a relatively large body of hot water, the layer of wax being used to form a glove over an extremity passed therethrough into the water.

At least one or more of the foregoing objects, as well as the advantages thereof over existing and prior art forms, which will be apparent in view of the detailed specification, are accomplished by means hereinafter described and claimed.

In general, the present invention provides a method for providing therapeutic heat treatment to a body part comprising the steps of placing a suitable fluid in a container; placing wax in the container; heating the fluid and wax combination until the wax has melted forming a layer and the fluid has reached the treatment temperature; and passing the body part through the layer of wax and into the fluid to form a glove around the body part.

The present invention also provides for a kit for providing therapeutic heat treatment, the kit comprising a microwavable container; a removable lid; and a quantity of wax.

One exemplary method embodying the concepts of the present invention is disclosed. The description of this embodiment is deemed sufficient to effect a full disclosure of the subject invention, the exemplary embodiment being shown by way of example in the accompanying drawings and being described in detail without attempting to show all the various forms and modifications in which the invention might be embodied—the invention being measured by the appended claims and not by the details of the specification.

BRIEF DESCRIPTION OF THE DRAWINGS

FIG. 3 is a sectional side view of the container depicted in FIG. 2, with an extremity passing through the wax into the fluid; and FIG. 4 is a sectional side view of a container and lid having wax melting cages.

PREFERRED MODE FOR CARRYING OUT THE INVENTION

Figure 1:
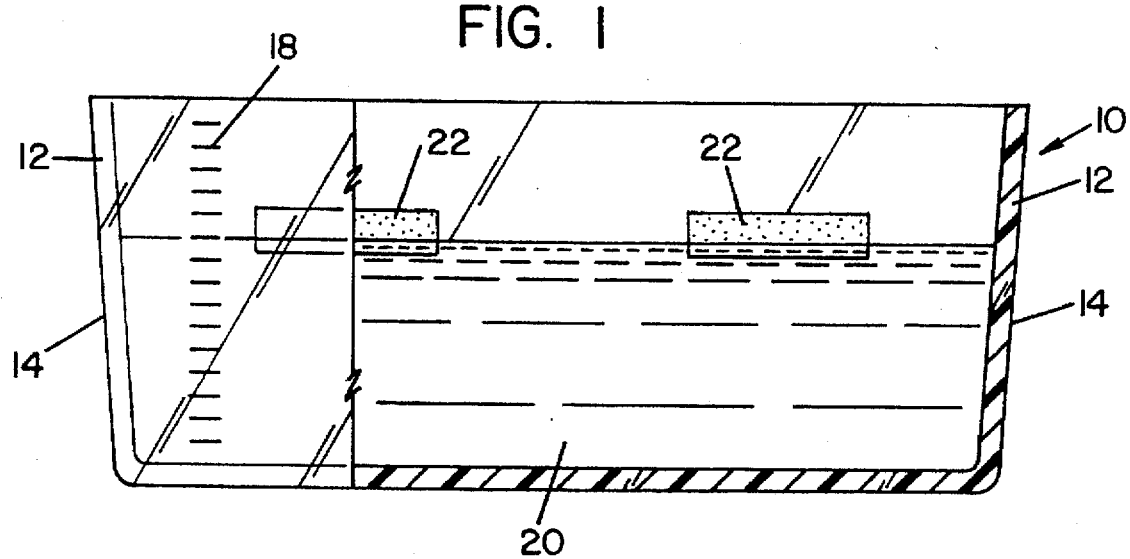
FIG. 1 is a sectional side view of a container holding a suitable fluid and two unmelted strips of wax.
Figure 2:
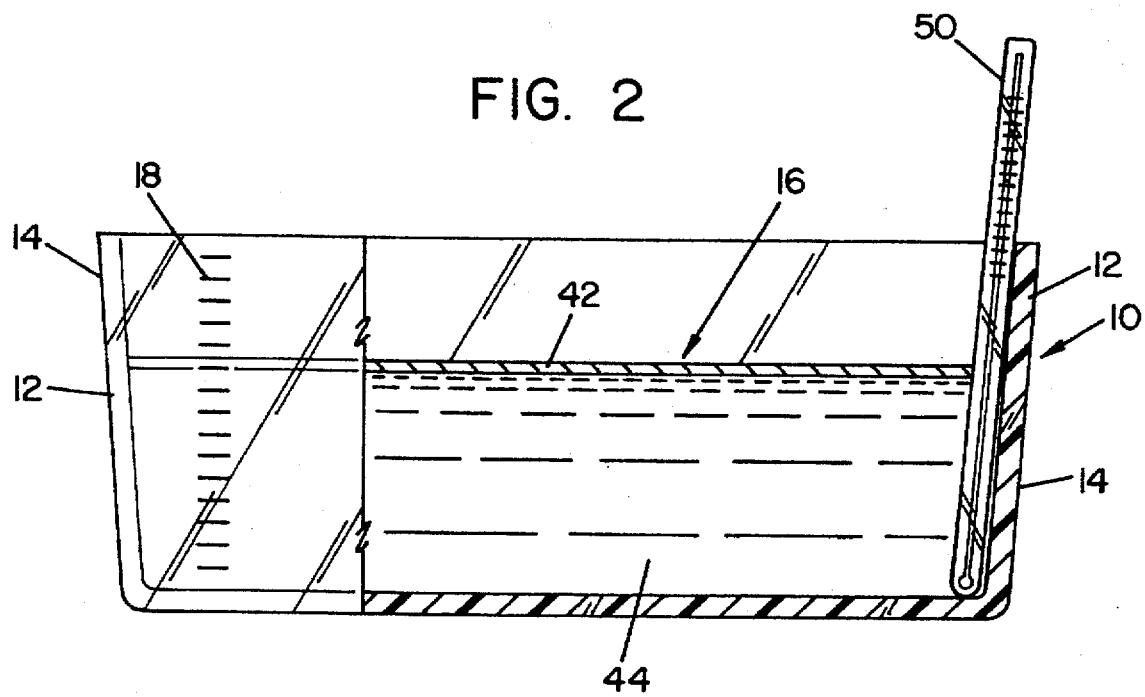
FIG. 2 is a sectional side view of the container depicted in FIG. 1, the fluid being heated and the wax being melted and stabilized.

A method for providing a therapeutic heat treatment according to the concepts of the present invention generally requires a microwavable container such as the one depicted in the figures and indicated generally by the numeral 10. The container 10 may be fabricated from one of the numerous known materials that are microwavable. It is desirable that the container have walls 12 thick enough to insulate the outer surface 14 of the container 10 from the heated combination 16 inside the container 10. A container 10 that has been found to be useful for implementing the method of the present invention to treat a hand is approximately 10 inches long by 6 inches wide and 4 inches deep. Other sizes would, of course, be used as needed for different extremities.

As will become apparent below, the container is provided to receive a volume of a suitable fluid and a wax or wax formulation, either of the latter providing a therapeutic covering or "glove" encompassing the hand or other body part immersed into the melted wax. While water is exemplified as the suitable fluid throughout this description, by "suitable" is meant that the fluid selected to receive the wax or wax formulation must meet several criteria. One of these is that the fluid must be microwave reactive, that is, it can be heated by exposure to microwave energy, and provide a fluid medium for melting the wax. Another is that the fluid should not be a solvent for the wax. Also, the fluid should be thermally stable and finally, it must not be harmful to the patient or user.

Next, while wax can be employed in practice of the present invention, wax formulations can also be. By "formulation" is meant wax or waxes that contain other therapeutic agents as will aid in the treatment and/or benefit the user. Such agents should be thermally stable, miscible with the wax, immiscible with the fluid and, capable of floating on the liquid with the wax, so as to become part of the covering encompassing the hand or other body part. As used throughout the specification and claims, the term wax is intended to include wax and waxes as well as wax formulations.

Returning now to the description of the container 10, it has a set of volume markings 18 on at least one wall 12 to inform the patient or caregiver how much fluid 20 is in the container 10. Strips of solid wax 22 are included with the container for each treatment. The strips of wax 22 are placed in the unheated fluid 20 before the water is heated. The quantity of wax 22 used for each treatment varies depending on the desired application. For instance, treating a foot may require more wax 22 than treating a hand.

The container 10 may have a lid, 30 depicted in FIG. 4, that cooperatively engages the container 10. The lid 30 includes a plurality of wax melting cages 32. Each cage 32 extends downwardly from the lid 30 into the container 10. The cages 32 are used to immerse strips of solid wax 22 at least partially in the fluid, or water 20, so that more surface area of the wax 22 is exposed to the water 20 as it is being heated. After the wax 22 has melted, the lid 30 is removed so that the extremity 40 may be placed in the container 10. The lid 30 may sealingly engage the container 10 or may loosely engage the container 10. When the lid 30 sealingly engages the container 10, vents 34 are provided in the lid 30 to permit any steam formed to escape.

In general, the method of the present invention is performed as follows. First, the patient or caregiver fills the container 10 with fluid 20 to the required level marker 18 as marked on the side 12 of the container 10. The patient then places a quantity of wax 22 into the fluid 20, preferably in the cages or otherwise submerged. The container 10 holding the combination 16 is then placed in a microwave oven (not shown). The oven is turned on for a length of time until the fluid 20 is heated to the treatment temperature, in turn, melting the wax 22. The heated combination 16 is then permitted to stand to allow the melted wax to stabilize. When the melted wax stabilizes, a layer of stabilized wax 42 is formed on top of the heated fluid 44. Once stabilized, the patient passes an extremity 40 to be treated through the layer of wax 42 and into the hot water 44. As the extremity passes through the wax layer 42, the wax coats the extremity 40 forming a wax glove 46 around the extremity.

The hand is then removed, allowing the wax to solidify. The hand is then reinserted through the layer of molten wax, causing more wax to be deposited on the hand, increasing the thickness of the wax glove and consequently depleting the "reservoir" of molten wax. The warm water is synonymous to the large volume of molten wax in the prior art. The water can be used to provide adjunct therapy, but the purpose is to warm the wax glove further. The "gloved" hand is, at some point, removed from the microwave wax bath, wrapped in a plastic sheet covered with a towel, as an insulation, and the heat therapy continued outside the bath, the therapeutic heat being provided by the wax glove "heat reservoir".

More specifically, for the treatment of a hand or a foot, the user or caregiver first places approximately 2000 grams of water 20, or other suitable fluid, in the container 10. Next, approximately 120 grams of wax 22 is placed in the water 20, as noted hereinabove. The container 10 is then placed in a microwave. The amount of time required to heat water and melt the wax 22 varies depending on the strength of the microwave, but it has been found that a 900 watt microwave will heat such a combination 16 in approximately 7½ minutes. Once the combination 16 is heated, the heated combination 16 is allowed to stand for approximately 2½ minutes to allow the wax to stabilize. The total time for preparing the treatment is thus approximately 10 minutes, significantly shorter than the time period to melt and stabilize the wax in the prior art. The main purpose of the fluid is that it allows the "non-microwavable" wax to be melted in the microwave.

Ideally the layer of stabilized wax 42 on top of the heated water 44 should have a depth of approximately 2 millimeters. It has been found that adding approximately 120 grams of wax to approximately 2000 grams of water in a 6 inch by 10 inch by 4 inch container 10 produces a layer of stabilized wax 42 having a depth of approximately 2 millimeters. When containers are used having different dimensions, the volume of wax must be altered accordingly.

It has also been found that when the combination 16 of the wax 22 and water 20 is heated in a microwave other than a 900 watt microwave, the amount of time for melting the wax 22 and heating the water 20 increases but the time to stabilize the wax decreases. Thus, the total time remains approximately 10 minutes. For instance, an 800 watt microwave takes approximately 8½ minutes to heat the water 20 and melt the wax 22, but only 1½ minutes to stabilize the melted wax. A 750 watt microwave requires approximately 9 minutes to heat the water 20 and melt the wax 22, but only 1 minute is require to stabilize the melted wax. A 700 watt microwave requires 9½ minutes to heat the water 20 and melt the wax 22 but only ½ minute to acquire wax stabilization. When higher or lower power microwaves are used, the overall time may vary accordingly. Similarly, the power and overall time may range within other parameters where the suitable fluid is other than water.

A thermometer 50 is provided to allow the patient to determine the temperature of the heated water 44. The patient continues to heat the combination 16 until the water 20 is approximately 130 degrees Fahrenheit. To do so, the patient heats the combination 16 for approximately 7 minutes, measures the temperature, and reheats for approximately 1 minute. The patient then measures the temperature of the water 20 again and repeats the 1 minute heatings until the water 44 is approximately 130 degrees Fahrenheit.

When the wax stabilizes, it cools and forms an insulating barrier over the heated water 44. The stabilized wax 42 also helps keep the water 44 hot enough to provide the beneficial treatment. As the extremity 40 is passed through the layer of stabilized wax 42, the wax 42 sticks to the skin forming a wax glove 46 around the extremity. The layer of wax 46 is thin enough to allow the extremity to feel the heat of the water 44 but thick enough to protect the skin from the 130 degree water. The extremity 40 can be passed into the water 44 to provide additional heat, if desired. The beneficial effects of the heat last approximately ten to thirty minutes.

As will be understood from the foregoing description of the operation of the invention, a kit, referred to generally by the numeral 60, can be provided for convenient and ready practice of the method of therapeutic heat treatment, according to the present invention. The kit, depicted in FIG. 5, comprises the container 10, with its lid 30 and the requisite amount of wax for one treatment. The thermometer 50 may also be included, inside the container. The kit can be suitably sealed subsequent to manufacture to assure the safety and quality of its contents. Appropriate instructions can also be provided in sheet form or on a disposable packaging (not shown). The user will open the kit, remove the lid, and add the required volume of water to the container and then proceed as described hereinabove. After use, the entire unit can be discarded, re-used or cleaned and stored for subsequent usage. Additional quantities of wax in strip form or otherwise can be packaged with the kit for multiple uses or, these can be separately purchased as refills, depending upon the marketing strategy desired.

Based upon the foregoing description, it should be apparent that a method for applying a therapeutic heat treatment according to the concepts of the present invention effectively and quickly applies heat to an extremity using a small quantity of wax. It is to be appreciated that the preferred method of placing the wax within cages, carried by the removable lid, for partial immersion in the water prior to heating is by no means to be construed as limiting. Thus, it is within the scope of the present invention to practice the method without the lid, in which instance the wax can merely be floated upon the surface of the water during the heating and melting step. However, due to the decreased area acted upon by the heating water, the time for melting will be increased.

It is also within the scope of the present invention to provide lower melting waxes or formulations. The lowered temperature of the combination wax water may be desirable in some therapies such as burn patients who require therapeutic effects of wax therapy, but must not be exposed to "high" temperatures. Also persons with higher sensitivity to heat may require lower temperature systems. Finally, it is within the scope of the present invention to employ a suitable fluid other than water as the medium for melting the wax or wax formulation, as discussed hereinabove.

It is thus evident that all variations fall within the scope of the claimed invention; therefore, the selection of specific material components as well as method steps can be determined without departing from the spirit of the present invention. Moreover, the scope of the present invention shall include all modifications and variations that may fall within the scope of the attached claims.

What is claimed is:

1. A method for providing therapeutic heat treatment to a body part, said method comprising the steps of:

placing a suitable fluid in a container;

placing wax in the container to form a fluid and wax combination;

heating said fluid and wax combination until the wax has melted forming a layer and said fluid has reached a treatment temperature; and passing the body part through said wax layer into said fluid to form a glove around the body part.

2. A method according to claim 1, further comprising the step of stabilizing said wax after said fluid has been melted.

3. A method according to claim 1 wherein said glove has a thickness and including the additional step of passing the body part through said wax layer into said fluid at least a second time, thereby increasing the thickness of said wax glove around the body part.

4. A method according to claim 3, further comprising the step of holding said wax glove and the body part in said fluid until said fluid has cooled.

5. A method according to claim 3, further comprising the step of removing the body part and said wax glove and wrapping said body part and said wax glove with an insulating material to retain the heat of said glove, thereby providing the therapeutic heat treatment.

6. A method according to claim 1, wherein the volume of said wax is in an approximate range of 3 to 10 percent the volume of said fluid.

7. A method according to claim 1, wherein the weight of said fluid is approximately 2000 grams and the weight of said wax is approximately 120 grams.

8. A method according to claim 1, wherein said combination is heated in a microwave oven.

9. A method according to claim 1, wherein said fluid is heated until the temperature thereof is approximately 130 degrees Fahrenheit.

10. A method according to claim 1, including the further steps of:

providing a lid for said container, said lid carrying at least one wax melting cage from an underside of said lid;

placing said wax in said cage; and placing said lid upon said container prior to said step of heating.

11. A method according to claim 10, wherein said lid provides a plurality of said wax melting cages, said cages being structured to at least partially immerse said wax in said fluid.

12. A method according to claim 11, wherein said wax is provided in strip form and said strips are at least partially immersed in said fluid vertically.

13. A therapeutic heat treatment kit, said kit comprising:

a microwavable container;

a removable lid; said lid providing at least one wax melting cage extending from an underside of said lid; and a quantity of wax.

14. A therapeutic heat treatment kit according to claim 13, wherein said cage is structured to immerse said wax in fluid provided in said container.

15. A therapeutic heat treatment kit according to claim 14, wherein said wax is provided in strip form and said strips are immersed in said fluid vertically.

16. A therapeutic heat treatment kit according to claim 15, wherein said lid provides a plurality of said cages.

17. A therapeutic heat treatment kit according to claim 13, further comprising a thermometer.

18. A therapeutic heat treatment kit according to claim 13, wherein said quantity of wax is approximately 120 grams per treatment.

19. A therapeutic heat treatment kit according to claim 13, wherein said container has fluid volume markings disposed on at least one wall thereof.

* * * * *